United States Patent [19]

Perronnet et al.

[11] 4,069,319

[45] Jan. 17, 1978

[54] NOVEL THIADIAZOLES

[75] Inventors: Jacques Perronnet, Paris; Laurent Taliani, Les Pavillons-sous-Bois, both of France

[73] Assignee: Roussel UCLAF, Paris, France

[21] Appl. No.: 721,373

[22] Filed: Sept. 8, 1976

Related U.S. Application Data

[63] Continuation of Ser. No. 517,379, Oct. 23, 1974, abandoned.

[30] Foreign Application Priority Data

Oct. 26, 1973 France ............................... 73 38223

[51] Int. Cl.$^2$ .................. A61K 31/425; C07D 285/08
[52] U.S. Cl. ............................ 424/200; 260/302 SD; 260/302 D; 260/302 E; 260/306.8 D
[58] Field of Search ............... 260/302 E, 306.8 D; 424/200

[56] References Cited

U.S. PATENT DOCUMENTS

| | | | |
|---|---|---|---|
| 3,574,223 | 4/1971 | Ratz et al. | 260/302 E |
| 3,801,586 | 4/1974 | Barker et al. | 260/302 E |
| 3,943,144 | 3/1976 | Meyer et al. | 260/302 E |

*Primary Examiner*—Richard J. Gallagher
*Attorney, Agent, or Firm*—Hammond & Littell

[57] ABSTRACT

Novel thiadiazoles of the formula

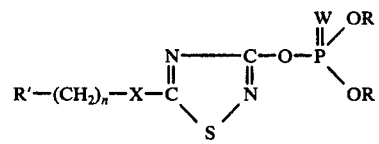

wherein R is alkyl of 1 to 3 carbon atoms, W is selected from the group consisting of oxygen and sulfur, X is selected from the group consisting of —O—, —S— and

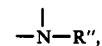

R" is selected from the group consisting of hydrogen and alkyl of 1 to 3 carbon atoms, $n$ is 1, 2, 3 or 4 and R' is selected from the group consisting of hydrogen, —CN, alkoxy of 1 to 3 carbon atoms, alkoxycarbonyl of 2 to 4 carbon atoms, alkenyl of 2 to 4 carbon atoms, phenyl optionally substituted with one member of the group consisting of halogen, alkyl of 1 to 3 carbon atoms and alkoxy of 1 to 3 carbon atoms or substituted with two members of the group consisting of halogen, alkyl of 1 to 3 carbon atoms and alkoxy of 1 to 3 carbon atoms, having insecticidal and nematocidal activity.

24 Claims, No Drawings

ND THIADIAZOLES

PRIOR APPLICATION

This application is a continuation of our copending commonly assigned U.S. patent application Ser. No. 517,379 filed Oct. 23, 1974, now abandoned.

OBJECTS OF THE INVENTION

It is an object of the invention to provide the novel thiadiazoles of formula I and to provide a novel process for their preparation.

It is another object of the invention to provide novel pesticidal compositions.

It is an additional object of the invention to provide a novel method of combatting insects and a novel method of combatting nematodes.

These and other objects and advantages of the invention will become obvious from the following detailed description.

THE INVENTION

The novel thiadiazoles of the invention have the formula

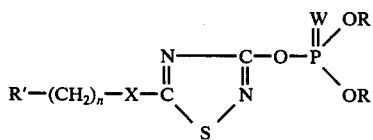

wherein R is alkyl of 1 to 3 carbon atoms, W is selected from the group consisting of oxygen and sulfur, X is selected from the group consisting of —O—, —S— and

R" is selected from the group consisting of hydrogen and alkyl of 1 to 3 carbon atoms, n is 1,2,3 or 4 and R' is selected from the group consisting of hydrogen, —CN, alkoxy of 1 to 3 carbon atoms, alkoxycarbonyl of 2 to 4 carbon atoms, alkenyl of 2 to 4 carbon atoms, phenyl optionally substituted with one member of the group consisting of halogen, alkyl of 1 to 3 carbon atoms and alkoxy of 1 to 3 carbon atoms or substituted with two members of the group consisting of halogen, alkyl of 1 to 3 carbon atoms and alkoxy of 1 to 3 carbon atoms.

The preferred compounds of formula I are those where R is alkyl such as propyl or isopropyl but preferably ethyl or methyl, X is

where R" is hydrogen or propyl, isopropyl, ethyl and preferably methyl, R' is (1) alkoxycarbonyl where the alkoxy is propoxy, isopropoxy, methoxy and preferably ethoxy; (2) alkoxy such as propoxy, isopropoxy, methoxy and preferably ethoxy; (3) alkenyl such as 2-methyl-1-propenyl, 1-methyl-1-propenyl, 2-methyl-2-propenyl, 1-methyl-2-propenyl, 1-butenyl, 2-butenyl, 3-butenyl, allyl, isopropenyl, 2-methyl-vinyl and preferably vinyl; (4) phenyl optionally mono substituted in the meta, ortho and preferably para position with isopropoxy, propoxy, ethoxy, methoxy, isopropyl, propyl, ethyl, methyl, iodine, bromine, fluorine and preferably chlorine or phenyl disubstituted with isopropoxy, propoxy, ethoxy, methoxy, isopropyl, propyl, ethyl, methyl, iodine, bromine, fluorine and preferably chlorine.

In the most preferred compounds of formula I, R is methyl or ethyl, X is oxygen, sulfur or amino methyl, n is 1, 2 or 4 and R' is hydrogen, p-chlorophenyl, phenyl, vinyl, p-tolyl or o,p-dichlorophenyl.

The novel process of the invention for the preparation of thiadiazoles of formula I comprises cyclizing a compound of the formula

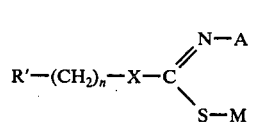

wherein R', X and n have the above definitions, A is cyano or alkoxycarbonyl and M is hydrogen or an alkali metal, in the presence of an oxidant when A is cyano or in the presence of ammonia and an alkali metal hypohalite when A is alkoxycarbonyl to obtain a compound of the formula

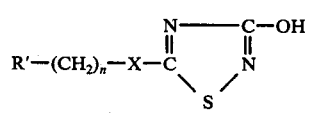

and reacting the latter with a compound of the formula

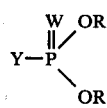

where Y is halogen and R and W have the above definition to obtain the corresponding compound of formula I.

The oxidant is preferably hydrogen peroxide but may be bromine in an aqueous media or an organic peracid such as peracetic acid, monoperphthalic acid or perbenzoic acid. The alkali metal hypohalite is preferably sodium hypochlorite but may also be potassium hypochlorite or sodium or potassium hypobromite. The condensation of the compounds of formulae II and III is preferably effected in a solvent such as acetone or acetonitrile and in the presence of a base such as triethylamine or an alkali metal carbonate.

The starting materials of formula II which are not known may be prepared by one of the following methods which have been illustrated in the examples. When X is sulfur, a compound of the formula

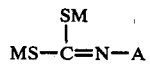

is reacted with a compound of the formula R'—(CH$_2$)$_n$—Z wherein M, A, R' and n have the above definitions and Z is an electronegative group such as halogen or R'—(CH$_2$)$_n$—SO$_4$—.

When X is oxygen, a compound of the formula A—NH₂ is reacted with an Xanthic ester of the formula

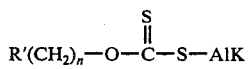

wherein A, R' and n have the above definitions and AlK is alkyl of 1 to 3 carbon atoms and then the product is reacted with an alkali metal alcoholate.

When X is nitrogen, a compound of the formula S=C=N-A where A is alkoxycarbonyl is reacted with an amine of the formula R'—(CH₂)ₙ—NH—AlK' wherein A, R' and n have the above definitions and AlK' is alkyl of 1 to 3 carbon atoms.

The novel pesticidal compositions of the invention are comprised of an effective amount of at least one compound of formula I and a carrier. The compositions may be in the form of powders, granules, suspensions, emulsions or solutions containing the active material in admixture, for example, with a vehicle and/or an anionic, non-ionic or cationic surface active agent to ensure a uniform dispersion of the substances in the composition. The vehicle may be a liquid such as water, alcohols, hydrocarbons or other organic solvents, an animal, vegetable or mineral oil or a powder such as talc, clays, silicates or kieselguhr.

The pesticidal compositions possess good insecticidal activity against insects such as *Prodenia litura, Drosophila melanogaster, Blatella germanica, Sitophilus granarius* and *Tribolium confusum* and a good nematocidal activity against nematodes such as Panagrellus Silusiae and Ditylenchus Miceliophagus.

Insecticidal liquids or powders for foliar spraying preferably contain 10 to 80% by weight of the compound of formula I. An example of an insecticidal emulsifiable concentrate is 15% by weight of 3-(diethoxythiophosphoryloxy)-5-(p-chlorobenzylthio)-1,2,4-thiadiazole, 6.4% of Atlox 4851 (oxyethylene triglyceride combined with a sulfonate with an acid No. of 1.5), 3.2% of Atlox 4855 (oxyethylene triglyceride combined with a sulfonate with an acid No. of 3) and 75.4% by weight of xylene.

The novel pesticidal method of the invention comprises contacting insects or nematodes with a lethal amount of at least one compound of formula I.

In the following examples there are described several preferred embodiments to illustrate the invention. However, it should be understood that the invention is not intended to be limited to the specific embodiments.

EXAMPLE 1

3-(diethoxythiophosphoryloxy)-5-methylthio-1,2,4-thiadiazole

STEP A: 3-hydroxy-5-methylthio-1,2,4-thiadiazole

A mixture of 80 g of dipotassium N-cyano-dithioimidocarbonate and 50.4g of dimethyl sulfate in 500 ml of water stood at room temperature for 2 hours and was then filtered. 44 ml of 30% hydrogen peroxide were added dropwise to the filtrate which was then acidified with 40 ml of concentrated hydrochloric acid. The mixture was cooled on an ice bath and the crystals formed were recovered by vacuum filtration, were washed with water and dried to obtain 36 g of 3-hydroxy-5-methylthio-1,2,4-thiadiazole melting at 160° C.

STEP B: 3-(diethoxythiophosphoryloxy)-5-methylthio-1,2,4-thiadiazole

A mixture of 7.6 g of the product of Step A, 9.5 g of diethyl chlorothiophosphate and 7 g of potassium carbonate in 50 ml of acetone was stirred overnight at room temperature and the mixture was then filtered. The filtrate was concentrated by evaporation under reduced pressure and was chromatographed over silica. Elution with a 9-1 benzene-ethylacetate mixture yielded 3-(diethoxythiophosphoryloxy)-5-methylthio-1,2,4-thiadiazole with a refractive index of $n_D^{20} = 1.5534$ and Rf=0.4.

EXAMPLE 2

3-(dimethoxythiophosphoryloxy)-5-methylthio-1,2,4-thiadiazole

The procedure of Step B of Example 1 was repeated using dimethyl chlorothiophosphate to obtain 3-(dimethoxythiophoryloxy)-5-methylthio-1,2,4-thiadiazole with a melting point of 45° C.

EXAMPLE 3

3-(diethoxythiophosphoryloxy)-5-ethylthio-1,2,4-thiadiazole

Using the procedure of Step A of Example 1, diethyl sulfate was reacted in the presence of acetic acid to obtain 3-hydroxy-5-ethylthio-1,2,4-thiadiazole melting at 129° C.

Using the procedure of Step B of Example 1, 3-hydroxy-5-ethylthio-1,2,4-thiadiazole was reacted which after chromatography with benzene as eluant yielded 3-(diethoxythiophosphoryloxy)-5-ethylthio-1,2,4-thiadiazole with a refractive index of $n_D^{20} = 1.5325$ and an Rf=0.35.

EXAMPLE 4

3-(diethoxythiophosphoryloxy)-5-p-chlorobenzylthio-1,2,4-thiadiazole

A mixture of 80 g of dipotassium N-cyano-dithioimidocarbonate, 64.9 g of p-chlorobenzyl chloride, 400 ml of methanol and 400 ml of water was stirred for 5 hours and the solvents were evaporated. The residue was crystallized from ethanol to obtain monopotassium S-p-chlorobenzyl N-cyano-dithioimidocarbonate with a melting point of 250° C (dec).

144 g of the said product and 48 ml of 30% hydrogen peroxide in 1 liter of water were heated to 65° C and then returned to room temperature. The solution was filtered and the filtrate was acidified with 40 ml of concentrated hydrochloric acid. The crystals formed were recovered by filtration, washed with water and dried to obtain 90 g of 3-hydroxy-5-(p-chlorobenzylthio)-1,2,4-thiadiazole which after crystallization from ethyl acetate melted at 138° C.

Using the procedure of Step B of Example 1, the latter product was reacted and after chromatography with a 9-1 cyclohexane-ethyl acetate eluant, there was obtained 3-(diethoxythiophosphoryloxy)-5-p-chlorobenzylthio-1,2,4-thiadiazole with a refractive index $n_D^{20} = 1.590$ and Rf = 0.4.

EXAMPLE 5

3-(dimethoxythiophosphoryloxy)-5-(p-chlorbenzylthio)-1,2,4-thiadiazole

Using the procedure of Step B of Example 1, 3-hydroxy-5-p-chlorobenzylthio-1,2,4-thiadiazole and dimethyl chlorothiophosphate were reacted to obtain 3-(dimethoxythiophosphoryloxy)-5-p-chlorobenzylthio-1,2,4-thiadiazole with a refractive index of $n_D^{20} = 1.605$ and Rf = 0.35.

EXAMPLE 6

3-(dimethoxythiophosphoryloxy)-5-dimethylamino-1,2,4-thiadiazole 180 ml of a solution of 10% dimethylamine in ether were added to a solution of 40 g of ethoxycarbonyl isothiocyanate in 200 ml of benzene and the reaction mixture was stirred for 15 minutes at 20–25° C. The solvent and excess dimethylamine were evaporated and the resulting oil was crystallized to obtain N,N-dimethyl-N-ethoxycarbonyl thiourea melting at 66° C. Rf = 0.25 [silica/benzene-ethyl acetate (9-1)].

A solution of 43 g of N,N-dimethyl-N-ethoxycarbonylthiourea, 25 ml of sodium hydroxide solution, 250 ml of water and a 1 M solution of sodium hypochlorite were added simultaneously to 450 ml of a concentrated ammonium hydroxide solution at 0° to 5° C and the reaction mixture was stirred for 2 hours at 0° to 5° C and then 3 hours at room temperature. The mixture was evaporated to the point of solidification of the mass which was then adjusted to a pH of 4 with concentrated hydrochloric acid. The solution was extracted with chloroform and the organic phase was dried over magnesium sulfate and was evaporated to dryness. The crystals were washed with petroleum ether (b.p. 40-75° C) to obtain 11 g of 3-hydroxy-5-dimethylamino-1,2,4-thiadiazole melting at 142° C and Rf (1-1acetone - CHCl₃) = 0.2.

A mixture of 0.366 g of the latter product, 0.3 ml of dimethyl chlorothiophosphate and 0.35 g of potassium carbonate in 10 ml of acetone was stirred for 16 hours at room temperature and was then filtered. The filtrate was concentrated by evaporation and the residue was chromatographed over silica. Elution with a 6-4 ethylacetate-cyclohexane yielded 3-(dimethoxythiophosphoryloxy)-5-dimethylamino-1,2,4-thiadiazole with an Rf = 0.45.

EXAMPLE 7

3-(diethoxythiophosphoryloxy)-5-dimethylamino-1,2,4-thiadiazole

Using the procedure of Example 6, diethyl chlorothiophosphate and 3-hydroxy-5-dimethylamino-1,2,4-thiadiazole were reacted and after chromatography and elution with an 8-2benzene-ethylacetate mixture, there was obtained 3-(diethoxythiophosphoryloxy)-5-dimethylamino-1,2,4-thiadiazole with a melting point of 48° C and Rf=0.55.

EXAMPLE 8

3-(diethoxythiophosphoryloxy)-5-ethoxy-1,2,4-thiadiazole 200 g of O-ethyl monopotassium N-cyano-thioimidocarbonate was added to 800 ml of water and 130 ml of 30% hydrogen peroxide were added thereto in 10 ml fractions. The mixture stood at room temperature and then 30 g of sodium bicarbonate were added. The solution was washed with 500 ml of ethylacetate and the pH was then adjusted to 3 with concentrated hydrochloric acid. The mixture was extracted with ethylacetate and the extracts were dried over sodium sulfate and then evaporated to dryness. The 85 g of oil residue were crystallized from 200 ml of ether and then from benzene to obtain 28 g of 3-hydroxy-5-ethoxy-1,2,4-thiadiazole melting at 98° C.

A mixture of 14.6 g of the latter product, 19 g of diethyl chlorothiophosphate and 14 g of potassium carbonate in 200 ml of acetonitrile was stirred for 40 hours at room temperature. The reaction mixture was then filtered and the filtrate was evaporated to dryness. The residue was chromatographed over silica and was eluted with benzene (Rf=0.3) to obtain 19 g of 3-(diethoxythiophosphoryloxy)-5-ethoxy-1,2,4-thiadiazole with a refractive index of $n_D^{20} = 1.503$.

EXAMPLE 9

3-(dimethoxythiophosphoryloxy)-5-ethylthio-1,2,4-thiadiazole

Using the procedure of Example 3, dimethyl chlorothiophosphate and 3-hydroxy-5-ethylthio-1,2,4-thiadiazole were reacted to obtain 3-(dimethoxythiophosphoryloxy)-5-ethylthio-1,2,4-thiadiazole with a refractive index of $n_D^{20} = 1.559$ and Rf=0.5.

EXAMPLE 10

3-(dimethoxythiophosphoryloxy)-5-ethylthio-1,2,4-thiadiazole

Using the procedure of Example 9, dimethyl chlorothiophosphate was reacted to obtain 3-(dimethoxythiophosphoryloxy)-5-ethylthio-1,2,4-thiadiazole with an Rf=0.2 (silica 4-6 cyclohexane-ethylacetate).

EXAMPLE 11

3-(dimethoxythiophosphoryloxy)-5-p-chlorobenzylthio-1,2,4-thiadiazole

Using the procedure of Example 4, dimethyl chlorothiophosphate and 3-hydroxy-5-p-chlorobenzylthio-1,2,4-thiadiazole were reacted to form 3-(dimethoxythiophosphoryloxy)-5-p-chlorobenzylthio-1,2,4-thiadiazole with a refractive index of $n_D^{20} = 1.5885$.

EXAMPLE 12

3-(diethoxythiophosphoryloxy)-5-benzylthio-1,2,4-thiadiazole

A mixture of 194.4 of dipotassium N-cyano-dithioimidocarbonate, 150 ml of water, 1 liter of methanol and 126.7 g of benzyl chloride was stirred at room temperature for 1 hour and after filtering, methanol was evaporated from the filtrate 2.5 liters of water were added again to the residue and then 110 ml of 30% hydrogen peroxide were slowly added. The mixture was stirred for one half hour at 40° C and then 15 hours at 20° C. The mixture was acidified with hydrochloric acid and was vacuum filtered. The precipitate was crystallized from toluene to obtain 80 g of 3-hydroxy-5-benzylthio-1,2,4-thiadiazole melting at 125° C.

22.4 g of the latter product and diethyl chlorothiophosphate were reacted by the procedure of Step B of Example 1 and acetonitrile was used to obtain 10.5 g of 3-(diethoxythiophosphoryloxy)-5-benzylthio-1,2,4-thiadiazole having a melting point of <50° C.

EXAMPLE 13

3-(diethoxythiophosphoryloxy)-5-allylthio-1,2,4-thiadiazole

Using the procedure of Example 12, 195 g of dipotassium N-cyanodithioimidocarbonate and 77 g of allyl chloride were reacted and then were treated with 100 ml of 30% hydrogen peroxide to obtain 63 g of 3-hydroxy-5-allythio-1,2,4-thiadiazole melting at 84° C.

8.7 g of the latter product were the reacted as in Example 12 to obtain 13 g of 3-(diethoxythiophosphoryloxy)-5-allylthio-1,2,4-thiadiazole with a refractive index of $n_D^{20} = 1.5525$.

EXAMPLE 14

3-(diethoxythiophosphoryloxy)-5-p-methylbenzylthio-1,2,4-thiadiazole

Using the procedure of Example 12, 58.2 g of dipotassium N-cyanodithioimidocarbonate and 42 g of p-methylbenzyl chloride were reacted and then were treated with 35 ml of 30% hydrogen peroxide to obtain 26 g of 3-hydroxy-5-p-methylbenzylthio-1,2,4-thiadiazole melting at 144° C.

Using the procedure of Example 12, 23.8 g of the resulting product were reacted in the presence of 10.1 g of triethylamine to obtain 10.5 g of 3-(diethoxythiophosphoryloxy)-5-p-methylbenzylthio-1,2,4-thiadiazole melting at <50° C.

EXAMPLE 15

3-(diethoxythiophosphoryloxy)-5-p-chlorobenzyloxy-1,2,4-thiadiazole 50 g of sodium hydride (50% suspension in mineral oil) was added over a one-half hour to a mixture of 142 g of p-chlorobenzyl alcohol and 1200 ml of tetrahydrofuran and the mixture was refluxed for 2 hours and then filtered. 76 g of carbon disulfide were added to the filtrate and the mixture was stirred at 20° C for one-half hour. The mixture was evaporated to dryness and the residue was taken up in ether and vacuum filtered to obtain 205 g of sodium O-p-chlorobenzyl dithiocarbonate melting at 250° C.

A mixture of 205 g of the latter product, 500 ml of benzene and 500 ml of methyl iodide was refluxed for 2½ hours and was then filtered. The filtrate was concentrated to dryness to obtain 196 g of methyl O-p-chlorobenzyl-dithiocarbonate.

200 g of the latter product were added to a solution of 34 g of cyanamide in 60 g of potassium methylate and 700 ml of ethanol and the mixture was stirred at 20° C for 17 hours. The mixture was vacuum filtered and the recovered crystals were washed with ether to obtain 126 of potassium O-p-chlorobenzyl N-cyano-thioimidocarbonate melting at 240° C.

Using the procedure of Example 12, 13 g of the latter product were reacted and treated with 6 ml of 30% hydrogen peroxide to obtain after crystallization from ethylacetate 2.4 g of 3-hydroxy-5-p-chlorobenzyloxy-1,2,4-thiadiazole melting at 170° C.

Using the procedure of Example 12, 2.5 g of the latter product was reacted with diethyl chlorothiophosphate to obtain 1.3 g of 3-(diethoxythiophosphoryloxy)-5-p-chlorobenzyloxy)-1,2,4-thiadiazole with a refractive index of $n_D^{20} = 1.5045$.

EXAMPLE 16

3-(diethoxythiophosphoryloxy)-5-n-butoxy-1,2,4-thiadiazole 380 g of carbon disulfide were added at 20°-30° C to a mixture of 280 g of potassium hydroxide pellets and 2.5 liters of n-butanol and after stirring the mixture for 2 hours, it was vacuum filtered The precipitate was washed with butanol and then ether to obtain 640 l g of potassium O-n-butyl dithiocarbonate melting at ≈ 260° C (dec). A mixture of 190 g of the latter product, 1 liter of benzene and 500 ml of methyl iodide was refluxed for 10 hours and then was filtered. The filtrate was evaporated to dryness and the residue was rectified to obtain 156 g of methyl O-n-butyl dithiocarbonate with a boiling point of 74° C at 0.5 mm Hg.

164 g of the latter product were added to a mixture of 42 g of cyanamide in a solution of 55 g of sodium methylate in 360 ml of methanol and 360 ml of ethanol at 20° C and the mixture was stirred at 20° C for 17 hours. The mixture was evaporated to dryness and the residue was washed with ether to obtain 120 g of sodium O-n-butyl N-cyanothioimidocarbonate melting at 240° C.

80 ml of 30% hydrogen peroxide were added to a mixture of 72 g of the latter product, 200 ml of water and 500 mg of phenolphthalein at 80° to 85° C and the pH was kept basic by addition of sodium hydroxide. The mixture was cooled and vacuum filtered to obtain the sodium salt of 3-hydroxy-5-n-butoxy-1,2,4-thiadiazole. The said salt was suspended in 100 ml of water which was then acidified with hydrochloric acid and extracted with ethyl acetate to obtain 58 g of 3-hydroxy -5-n-butoxy-1,2,4-thiadiazole melting at 62° C.

Using the procedure of Example 12, 8.8 g of the latter product were reacted with diethyl chlorothiophosphate to obtain 12 g of 3-(diethoxythiophosphoryloxy)-5-n-butoxy-1,2,4-thiadiazole with a refractive index of $n_D^{26} = 1.4960$.

EXAMPLE 17

3-(diethoxythiophosphoryloxy)-5-(2,4-dichlorobenzyl-thio)-1,2, 4-thiadiazole 72 g of 2,4-dichlorobenzyl chloride were added at 30° C to a mixture of 69.9 g of dipotassium N-cyanodithioimidocarbonate, 50 ml of water and 300 ml of methanol and the mixture was stirred at 30° C. for one-half hour. The methanol was evaporated under reduced pressure and 900 ml of water were added to the residue. 40 ml of 30% hydrogen peroxide were slowly added and the pH was kept basic by addition of potassium hydroxide. the mixture was stirred for 17 hours, was washed with ethyl acetate and was acidified with hydrochloric acid. The mixture was vacuum filtered and the precipitate was crystallized from toluene to obtain 32 g of 3-hydroxy-5-(2,4-dichlorobenzylthio)-1,2,4-thiadiazole melting at 134° C.

Using the procedure of Example 14, 29.3 g of the latter product was reacted with diethyl chlorothiophosphate to obtain 20 l g of 3-(diethoxythiophosphoryloxy)-5-(2,4-dichlorobenzylthio)-1,2,4-thiadiazole with a refractive index of $n_D^{26} = 1.5930$.

EXAMPLE 18

3-(diethoxythiophosphoryloxy)-5-methoxy-1,2,4-thiadiazole 60 ml of 30% hydrogen peroxide were slowly added at 70° C to a mixture of 46.2 g of potassium O-methyl N-cyanothioimidocarbonate [prepared from dimethyl dithiocarbamate, (Beilstein, Vol. 3, 208, I 83, II 151) as in Example 15 ] while keeping the pH at 8.4–8.6 by addition of potassium hydroxide and the mixture was washed with ether and acidified. The mixture was vacuum filtered to obtain 18 g of 3-hydroxy-5-methoxy-1,2,4-thiadiazole melting at 146° C.

Using the procedure of Step B of Example 1, 6.6 g of the latter product were reacted with 10 g of diethyl chlorothiophosphate to obtain 4.2 g of 3-(diethoxythiophosphoryloxy) -5-methoxy-1,2,4-thiadiazole with a refractive index of $n_D^{23} = 1.5114$.

EXAMPLE 19

3-(diethoxythiophosphoryloxy)-5-n-propoxy-1,2,4-thiadiazole 380 g of carbon disulfide were added to 20° C to a solution of 280 g of potassium hydroxide in 2 liters of propanol and the mixture was stirred for 2 hours and was vacuum filtered to obtain 624 g of potassium O-n-propyl dithiocarbonate melting at 230° C. 369 g of dimethyl sulfate were added to a solution of 429 g of the said product in 1 liter of water while keeping the temperture below 50° C. The mixture was stirred for 17 hours and the organic phase was decanted to obtain 338 g of methyl O-n-propyl dithiocarbonate with a boiling point of 60° C at 1 mm Hg and a refractive index of $n_D^{26} = 1.5385$.

338 g of the latter product were added over 15 minutes with stirring to a solution of 51.7 g of sodium in propanol and 94.6 g of cyanamide and stirring was maintained for 24 hours at 35° C under a current of inert gas. The mixture was concentrated to dryness to obtain 416 g of sodium O-n-propyl N-cyano dithiocarbonate.

The said product was dissolved in 1 liter of water and then 450 ml of 30% hydrogen peroxide were added thereto at 80° C over 2 hours while keeping the pH alkaline by addition of sodium hydroxide. The mixture was stirred for 24 hours, then cooled and washed with ethylacetate. The mixture was acidified by addition of hydrochloric acid and was vacuum filtered. The precipitate was washed with water and dried to obtain 200 g of 3-hydroxy-5-n-propoxy-1,2,4-thiadiazole melting at 92°0 C.

Using the procedure of Example 12, 24 g of the latter product and 28.3 g of diethyl chlorothiophosphate were reacted to obtain 17.5 g of 3-(diethoxythiophosphoryloxy)-5-n-propoxy-1,2,4-thiadiazole with a refractive index of $n_D^{26.5} = 1.5000$.

INSECTICIDAL ACTIVITY

A. Sitophilus granarius 0.2 μl of an acetone solution of the test compound was applied to the ventral thorax of each insect with 50 insects for each concentration of 500 or 500 ppm. The insects were held at 20° C and the readings were made 4, 24 and 48 hours and 5 and 6 days after treatments. The esults in Table I were expressed as the percent of mortality.

TABLE I

| % mortality after | Products of Examples | Concentration in mg/l 5000 | | | | 500 | | | |
|---|---|---|---|---|---|---|---|---|---|
| | | 9 | 11 | 13 | 16 | 9 | 11 | 13 | 16 |
| 4 hours | | | 100 | 100 | 100 | | 85 | 47 | 100 |
| 24 hours | | 100 | 100 | 100 | 100 | 82 | 85 | 50 | 100 |
| 48 hours | | 100 | | | | 80 | | | |
| 5 days | | | 100 | 100 | 100 | | 85 | 58 | 100 |
| 6 days | | 100 | | | | 80 | | | |

B. Tribolium confusum

The test procedure was the same as in test A with the product of Example 9 on Tribolium confusum and readings were taken 24 and 48 hours and 5 days after treatment. The results are reported in Table II.

TABLE II

| % mortality after | Concentrations in ppm | | |
|---|---|---|---|
| | 5000 | 2500 | 500 |
| 24 hours | 92.3 | 58.8 | 8 |
| 48 hours | 98.1 | 62.7 | 10 |
| 5 days | 96.2 | 60.8 | 8 |

C. Drosophila melanogaster

This test measured the activity of the vapors of the product and consisted of placing the insects in a Petri dish joined by a tergal screen to a crystallizer of the same diameter in which the test product was placed in acetone solution. The solvent was evaporated before the insects were introduced and 3 tests per concentration and 25 insects per test were run. The insects were about 48 hour old adults and the percent mortality was determined after 1,2,4,6 and 24 hours and the results are reported in Table III.

TABLE III

| % Mortality after hours | Products of Examples | Concentration in ppm 5000 | | | | 500 | | | | 50 | | | | 5 | | | |
|---|---|---|---|---|---|---|---|---|---|---|---|---|---|---|---|---|---|
| | | 9 | 11 | 13 | 16 | 9 | 11 | 13 | 16 | 9 | 11 | 13 | 16 | 9 | 11 | 13 | 16 |
| 1 | | | | | | | 63 | 0 | 100 | | | 0 | 77 | | | 0 | 25 |
| 2 | | 0 | | | | 19 | | | | 0 | | | | | | | |
| 4 | | 1.4 | | | | 30.2 | 92 | 100 | 100 | 0 | | 84 | 100 | | | 0 | 100 |
| 6 | | | | | | | 95 | 100 | 100 | | | 100 | 100 | | | 24 | 100 |
| 24 | | 84.3 | | | | 77.8 | | | | 2.4 | | | | | | | |

D. Prodenia litura (ingestion)

Prodenia litura caterpillars were introduced into closed plastic bottles containing on 8 mm diameter ring cut from a lettuce leaf, 4 μl of an acetone solution of the test product was placed on the leaf ring and 15 caterpillars about 10 days old were used for each treatment. 24 hours after treatment and the results are reported in Table VI.

TABLE VI

| % mortality after hours | Products of Example | Concentration in ppm 5000 | | | 2500 | | | 500 | | | 100 |
|---|---|---|---|---|---|---|---|---|---|---|---|
| | | 11 | 13 | 16 | 11 | 13 | 16 | 11 | 13 | 16 | |
| 1 | | 94 | 0 | 100 | 86 | 0 | 96 | 62 | 69 | 26 | |
| 24 | | 100 | 100 | 100 | 100 | 89 | 100 | 74 | 100 | 81 | |

The caterpillars were kept at 20° C in natural light with a 50% relative humidity and the individuals were maintained until after the treated ring was consumed. Readings were taken 1,24 and 48 hours after treatment to determine the percent mortality which is reported in Table IV.

TABLE IV

| Concentration in ppm | 500 | | 250 | | 125 | |
|---|---|---|---|---|---|---|
| Products of Examples | 4 | 16 | 4 | 16 | 4 | 16 |
| % mortality after hours | | | | | | |
| 1 | 0 | 0 | 0 | 0 | 0 | 0 |
| 24 | 80 | 20 | 60 | 30 | 60 | 0 |
| 48 | 100 | 100 | 100 | 70 | 80 | 30 |

*100% after 4 days of contact.

E. Male *Blatella germanica*

This test was effected by microcontact with male blattes germanica receiving a micro drop of an acetone solution of the test product between the second and third pair of feet. After the treatment, the insects were held in a dim light at 20° C and readings were made 24 and ?hours and 5 days after treatment. The results of Table V are expressed as percent of mortality.

TABLE V

| % Mortality after hours | Products of Example | Concentration in ppm 5000 | | | | 1250 | | | | 625 | | | | 312.5 | | | |
|---|---|---|---|---|---|---|---|---|---|---|---|---|---|---|---|---|---|
| | | 4 | 11 | 13 | 16 | 4 | 11 | 13 | 16 | 4 | 11 | 13 | 16 | 4 | 11 | 13 | 16 |
| 24 | | 63 | 100 | 94 | | 28 | 48 | 10 | 100 | | | | 85 | | | | 38 |
| 48 | | 95 | 100 | 100 | | 33 | 57 | 10 | 100 | | | | 100 | | | | 62 |
| 5 days | | 100 | 100 | 100 | | 65 | 90 | 20 | 100 | | | | 100 | | | | 95 |

F. Panagrellus Silusiae 0.5 ml of water containing about 2000 nematodes were placed in a pill-box containing 10 ml of an aqueous insecticidal composition of the test product and mortality readings were effected with a binocular magnifying glass 24 hours after treatment. 3 tests were run corresponding to a sample of 1 ml of solution in the test. The results were determined as the percent mortality for the product of Example 4 and the percent mortality after 24 hours was 100% at concentrations of 1 and 0.10 g/l.

G. Ditylenchus Myceliophagus

The test procedure was the same as in test F and the percent mortality for the product of Example 4 was 99% and 84%, respectively for concentrations of 1000 and 100 ppm.

H. *Musca domestica*

This test was a topical application to flies which received a micro drop of an acetone solution of the product applied to the dorsal thorax having been put to sleep with ether. The ensects were held at 20° C and a 50% relative humidity. They were fed with milk or water and readings of percent mortality were taken 1 hour and 24 hours after treatment and the results are reported in Table VI.

I. *Aphis fabae*

This test was effected by contact ingestion on a bean plant (*Vicia Faba*). After spraying with a solution of the test product to ensure a complete wetting of the plant which was then infested with 20 apterae per bean plant. Bean plants were surrounded by gauze to prevent the escape of the fleas. Readings of the living and dead as a function of time were taken and the % of Abbott efficacy is reported in Table VII.

TABLE VII

| % mortality after hours | Products of Example | Concentration in ppm 100 | | | 10 | | 1 |
|---|---|---|---|---|---|---|---|
| | | 11 | 13 | 16 | 13 | 16 | 16 |
| 2 | | 0 | 90 | 27 | 0 | 0 | 0 |
| 24 | | 23 | 100 | 100 | 17 | 0 | 0 |
| 48 | | 29 | 100 | 100 | 18 | 8 | 8 |

J. *Musca domestica larvae*

This contact-ingestion test consisted of placing 2ml of an acetone solution of the test product at different concentrations on 1 g of bran placed on a water glass. The solvent evaporated and then the treated bran was placed in a plastic bottle. 2 ml of milk were added thereto and after having a good mixing, the bottle was contaminated with 20 Musca domestica larvae aged 3 to 4 days. 3 tests were run for each concentration and the larvae were held at 20° C and 30% relative humidity. Readings of percent mortality were taken 48 hours and 8 days after treatment and the results are in Table VIII.

TABLE VIII

| % Mortality after hours | Products of Example | Concentration in ppm 5000 | | | 500 | | |
|---|---|---|---|---|---|---|---|
| | | 11 | 13 | 16 | 11 | 13 | 16 |
| 48 | | 82 | 41 | 92 | 41 | 38 | 59 |
| 8 days | | 90 | 90 | 100 | 49 | 77 | 90 |

Various modifications of the compositions and methods of the invention may be made without departing from the spirit or scope thereof and it is to be understood that the invention is to be limited only as defined in the appended claims.

We claim:

1. A compound of the formula

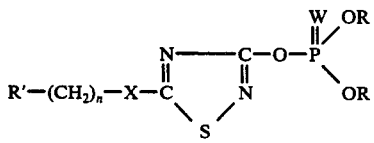

wherein R is alkyl of 1 to 3 carbon atoms, W is selected from the group consisting of oxygen and sulfur, X is selected from the group consisting of —O—, —S— and

R" is selected from the group consisting of hydrogen and alkyl of 1 to 3 carbon atoms, n is 1,2,3 or 4 and R' is selected from the group consisting of hydrogen, —CN, alkoxy of 1 to 3 carbon atoms, alkoxycarbonyl of 2 to 4 carbon atoms, alkenyl of 2 to 4 carbon atoms, phenyl optionally substituted with one member of the group consisting of halogen, alkyl of 1 to 3 carbon atoms and alkoxy of 1 to 3 carbon atoms or substituted with two members of the group consisting of halogen, alkyl of 1 to 3 carbon atoms and alkoxy of 1 to 3 carbon atoms.

2. A compound of claim 1 wherein R is selected from the group consisting of methyl and ethyl, X is selected from the group consisting of —O—, —S— and

n is 1 or 2 and R' is selected from the group consisting of hydrogen, p-chlorophenyl, phenyl, vinyl, p-tolyl and 2,4-dichlorophenyl.

3. The compound of claim 1 which is 3-(diethoxythiophosphoryloxy)-5-methylthio-1,2,4-thiadiazole.

4. The compound of claim 1 which is 3-(dimethoxythiophosphoryloxy)-5-methylthio-1,2,4-thiadiazole.

5. The compound of claim 1 which is 3-(diethoxythiophosphoryloxy)-5-ethylthio-1,2,4-thiadiazole.

6. The compound of claim 1 which is 3-(diethoxythiophosphoryloxy)-5-p-chlorobenzylthio-1,2,4-thiadiazole.

7. The compound of claim 1 which is 3-(dimethoxythiophosphoryloxy)-5p-chlorobenzylthio-1,2,4-thiadiazole.

8. The compound of claim 1 which is 3-(dimethoxythiophosphoryloxy)-5-dimethylamino-1,2,4-thiadiazole.

9. The compound of claim 1 which is 3-(diethoxythiophosphoryloxy)-5-dimethylamino-1,2,4-thiadiazole.

10. The compound of claim 1 which is 3-(diethoxythiophosphoryloxy)-5-ethoxy-1,2,4-thiadiazole.

11. The compound of claim 1 which is 3-(dimethoxythiophosphoryloxy)-5-ethylthio-1,2,4-thiadiazole.

12. The compound of claim 1 which is 3-(dimethoxyphosphoryloxy)-5-ethylthio-1,2,4-thiadiazole.

13. The compound of claim 1 which is 3-(dimethoxyphosphoryloxy)-5-p-chlorobenzylthio-1,2,4-thiadiazole.

14. The compound of claim 1 which is 3-(diethoxythiophosphoryloxy)-5-benzylthio-1,2,4-thiadiazole.

15. The compound of claim 1 which is 3-(diethoxythiophosphoryloxy)-5-allylthio-1,2,4-thiadiazole.

16. The compound of claim 1 which is 3-(diethoxythiophosphoryloxy)-5-p-methylbenzylthio-1,2,4-thiadiazole.

17. The compound of claim 1 which is 3-(diethoxythiophosphoryloxy)-5-p-chlorobenzyloxy-1,2,4-thiadiazole.

18. The compound of claim 1 which is 3-(diethoxythiophosphoryloxy)-5-n-butoxy-1,2,4-thiadiazole.

19. The compound of claim 1 which is 3-(diethoxythiophosphoryloxy)-5-(2,4-dichlorobenzylthio)-1,2,4-thiadiazole.

20. The compound of claim 1 which is 3-(diethoxythiophosphoryloxy)-5-methoxy-1,2,4-thiadiazole.

21. The compound of claim 1 which is 3-(diethoxythiophosphoryloxy)-5-n-propoxy-1,2,4-thiadiazole.

22. An insecticidal composition comprising an insecticidally effective amount of at least one compound of claim 1 and a carrier.

23. A method of combatting insects comprising contacting insects with an insecticidally effective amount of at least one compound of claim 1.

24. A method of combatting insects comprising contacting insects with an insecticidally effective amount of at least one compound of claim 2.

* * * * *